United States Patent [19]
Magatti et al.

[11] Patent Number: 4,803,206
[45] Date of Patent: Feb. 7, 1989

[54] ANTIHYPERTENSIVE ACYLPYRAZINES

[75] Inventors: Charles V. Magatti, Verona; Ronald J. Doll, Maplewood, both of N.J.

[73] Assignee: Schering Corporation, Kenilworth, N.J.

[21] Appl. No.: 164,594

[22] Filed: Mar. 7, 1988

[51] Int. Cl.⁴ .................. A61K 31/495; C07D 241/20
[52] U.S. Cl. .................................... 514/255; 514/242; 514/245; 514/252; 544/182; 544/212; 544/295; 544/357; 544/405; 544/407
[58] Field of Search ............... 544/405, 407, 182, 212, 544/295, 357; 514/252, 255, 242, 245

[56] References Cited
U.S. PATENT DOCUMENTS 3,544,568 12/1970 Cragoe, Jr. et al. ................ 544/405
4,041,032 8/1977 Murakami et al. .................. 544/407
4,550,111 10/1985 Barlow et al. ...................... 544/407

FOREIGN PATENT DOCUMENTS 0057572 8/1982 European Pat. Off. ............ 544/405

Primary Examiner—Richard L. Raymond
Assistant Examiner—James H. Turnipseed
Attorney, Agent, or Firm—Anita W. Magatti; James R. Nelson; Stephen I. Miller

[57] ABSTRACT

Acylpyrazines useful in the treatment of hypertension are disclosed.

14 Claims, No Drawings

ANTIHYPERTENSIVE ACYLPYRAZINES

SUMMARY

The present invention relates to acylpyrazines useful in the treatment of hypertension.

The present invention also relates to pharmaceutical compositions comprising said acylpyrazines and to a method of treating hypertension comprising administering said compounds or compositions to a mammal in need of such treatment.

DETAILED DESCRIPTION

Compounds of the present invention are represented by the formula

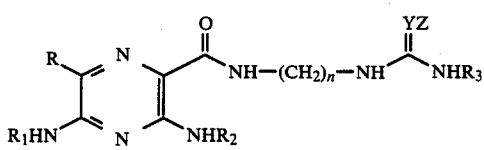

wherein
n is 2-6;
R is F, Cl, Br or I;
$R_1$ and $R_2$ are independently hydrogen or lower alkyl;
$R_3$ is hydrogen, lower alkyl, aryl, substituted aryl, heteroaryl, substituted heteroaryl, lower alkylaryl, substituted lower alkylaryl, lower alkylheteroaryl or substituted lower alkylheteroaryl;
Y is =CH— or =N—;
Z is hydrogen, cyano or carbamoyl when Y is =N—, and when Y is =CH—, Z is nitro;
and the pharmaceutically acceptable acid addition salts thereof.

As used herein, the term "lower alkyl" refers to straight or branched carbon chains of 1–6 carbon atoms. "Aryl" refers to an aromatic carbocyclic group of 6 to 10 ring carbon atoms in a single or fused ring system, e.g. phenyl and naphthyl, and "heteroaryl" refers to aromatic heterocyclic groups comprising 5 to 6 ring members wherein 1 to 3 ring members are heteroatoms selected from oxygen, nitrogen and sulfur, e.g. pyridyl, thienyl, furanyl and imidazolyl. All positional isomers, e.g. 2-pyridyl, 3-pyridyl and 4-pyridyl, are contemplated. "Substituted aryl" and "substituted lower alkylaryl" and "substituted heteroaryl" and "substituted lower alkylheteroaryl" refer to aryl, heteroaryl, lower alkylaryl and lower alkylheteroaryl groups wherein the aryl and heteroaryl groups may be substituted with 1–3 substituents selected from lower alkyl, lower alkoxy, halogeno (i.e., chloro, fluoro, bromo and iodo), amino, carboxy and lower alkoxy carbonyl. As used herein, "lower alkoxy" refers to alkoxy groups having 1–6 carbon atoms in a straight or branched chain.

Preferred compounds of formula I are those wherein n is 2. Also preferred are compounds of formula I wherein Y is =N—. Chloro and iodo substitution is preferred at R. $R^1$ and $R^2$ are preferably hydrogen, and $R^3$ is preferably hydrogen or lower alkyl.

More preferred are compounds wherein Y is =N— and Z is cyano. Especially preferred are compounds wherein n is 2, Y is =N— and Z is cyano. Also especially preferred are compounds wherein n is 2, Y is =N—, Z is cyano, $R_1$ and $R_2$ are each hydrogen and $R_3$ is hydrogen or lower alkyl.

The compounds of this invention have basic substituents (e.g. the nitrogens of the pyrazine ring) and form acid addition salts with organic and inorganic acids, e.g., HCl, HBr, $H_2SO_4$, methanesulfonic acid, toluenesulfonic acid, maleic acid, fumaric acid and camphorsulfonic acid. The non-toxic pharmaceutically acceptable salts are preferred.

The salts may be formed by conventional means, as by reacting the free base form of the product with one or more equivalents of the appropriate acid in a solvent or medium in which the salt is insoluble, or in a solvent such as water which is then removed in vacuo, or by exchanging the cations of an existing salt for another cation on a suitable ion exchange resin.

Compounds of this invention may exist in anhydrous form as well as hydrated forms. In general, the hydrated forms are equivalent to the anhydrous form for the purpose of the invention.

Compounds of formula I can be prepared by methods well known to those skilled in the art. For example, compounds of formula I wherein Y is =N— and Z is cyano can be prepared by reacting a pyrazine caboxylic acid of formula II with a cyanoguanidine of formula III:

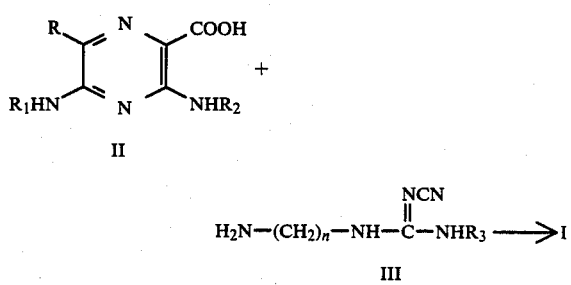

The reaction is carried out in an inert solvent such as dimethylformamide in the presence of a coupling agent such as 1,1'-carbonyldiimidazole. The resulting compound of formula I wherein Z is cyano may be hydrolyzed with an acid such as trifluoroacetic acid to prepare the corresponding compound wherein Z is carbamoyl. Alternatively, the cyano compound of formula IV may be hydrolyzed to the carbamoyl derivative before compounds of formula II and III are coupled.

Compounds of formula III can be prepared by reacting dimethylcyanodithioimide (IV) with an amine of formula V in an inert solvent in the presence of a base such as triethylamine, then reacting the product with a diamine of formula VI (e.g. diethylamine) to give a compound of formula III. The following reaction sequence exemplifies this procedure:

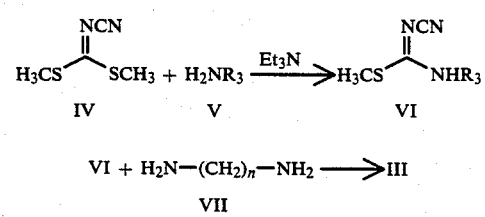

wherein n and $R_3$ are as defined above.

Compounds of formula I wherein Y is =N— and Z is hydrogen can be prepared by reacting an amine of formula VIII with a thiopseudourea such as that shown in formula IX:

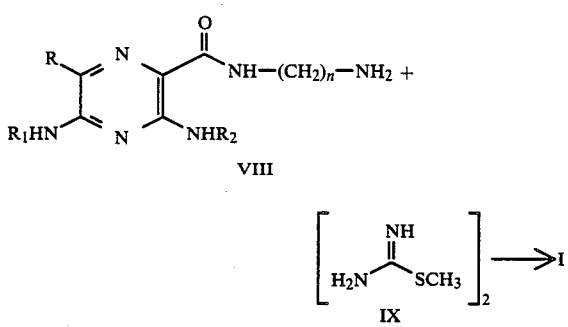

The reaction is carried out in a protic solvent such as water/methanol at elevated temperatures (e.g. on a steam bath).

Compounds of formula I wherein Y is =CH— and Z is nitro can be prepared according to the following reaction scheme:

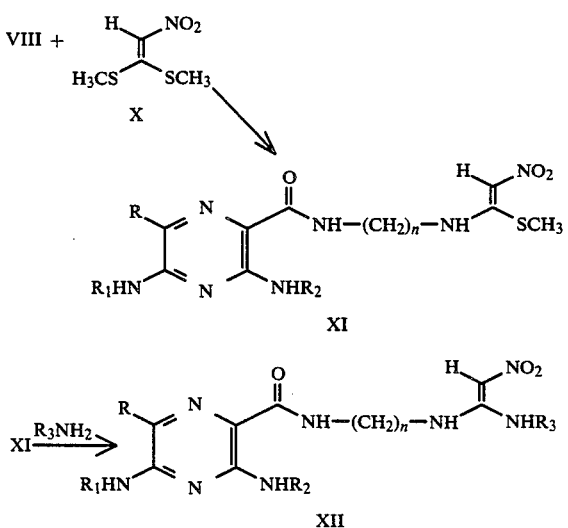

The reaction between the amine of formula VIII and 1,1-bis(methylthio)-2-nitroethylene (X) is carried out in a protic solvent such as isopropanol at elevated temperatures. The methylthio compound of formula XI is then converted to the product of formula XII by treating with the appropriate compound of formula $R_3NH_2$.

EXAMPLE 1

N-[2-[N'-methyl-N''-cyano)guanidino]ethyl]-3,5-diamino-6-chloropyrazine-2-carboxamide, hydrochloride Step 1: Add dimethylcyanodithioimide (5 g) to methylamine saturated methanol (MeOH) (10 ml) and stir at 0° C. for 2 hours. Filter the resultant solution and recrystallize the solid from ethanol (EtOH) to obtain N-cyano-N',S-dimethylisothiourea.

Step 2: Combine the product of Step 1 and ethylenediamine (4 ml) in acetonitrile ($CH_3CN$) (15 ml) and stir for 60 hours. Filter the resultant solution and recrystallize from EtOH to obtain N-methyl-N'-aminoethyl-N''-cyanoguanidine (15 g).

Step 3: Add 3,5-diamino-6-chloropyrazine-2-carboxylic acid (0.5 g) and 1,1-carbonyldiimidazole (CDI) (0.433 g) to dry dimethylformamide (DMF) (10 ml) and stir for 2 hours until precipitation is complete. Add the product of Step 2 (0.28 g) and stir for 48 hours. Evaporate the solvent in vacuo and partition the resultant residue between water and ethylacetate (EtOAc), extract the aqueous layer with diethyl ether ($Et_2O$), dry the organic layer over $MgSO_4$, filter and evaporate the solvent in vacuo. Chromatograph the resultant residue on a low pressure reversed phase column using $CH_3CN:H_2O$ as eluent, combine the desired fractions and evaporate the solvent. Dissolve the resultant residue in dilute hydrochloric acid (HCl) and evaporate the solvent to obtain the title compound (0.18 g). M.p. 239°-241° C.; $M^+=312$; elemental analysis: calculated value for $C_{10}H_{14}ClN_9O_4 \cdot HCl$ is C=34.49%, H=4.34%, N=36.20%, value found is C=34.72%, H=4.38%, N=36.19%.

EXAMPLE 2

N-[4-[(N'-methyl-N''-cyano)guanidino]butyl]-3,5-diamino-6-chloropyrazine-2-carboxamide Substitute N-methyl-N'-aminobutyl-N''-cyanoguanidine for the corresponding ethyl compound in Step 3 of Example 1 and proceed through the partitioning in EtOAc/$H_2O$. Separate the organic layer, wash with water and dry over $MgSO_4$. Filter and evaporate the solvent. Chromatograph the resultant residue, eluting with methylene chloride:MeOH, (4:1), to obtain the title compound as a yellow solid, $M^+=339$, thin layer chromatography $R_f=0.5$ ($CH_2Cl_2:CH_3OH$, 4:1).

EXAMPLE 3

N-[2-[(N'-carbamoyl-N''-methyl)guanidino]ethyl]3,5-diamino-6-chloropyrazine-2-carboxamide hydrochloride

Method 1

Combine the product of Example 1 (0.1 g) and trifluoroacetic acid (10 ml) and stir at room temperature for 18 hours. Evaporate the solvent and triturate the resultant residue in water. Filter and dry the solid, then redissolve the residue in 0.1N HCl. Evaporate the solvent and triturate the resultant residue in $Et_2O$. Decant the solution and dry the residue in vacuo to obtain the title compound.

Method 2

Step 1: Stir N-methyl-N'-aminoethyl-N''-cyanoguanidine (0.5 g) and 1N HCl (8 ml) for five days. Evaporate the solvent and recrystallize the resultant white solid from EtOH/water to obtain N-methyl-N'-aminoethyl-N''-carbamoyl guanidine.

Step 2: Follow the procedure of Example 1, Step 3 through the partitioning in EtOAc/$H_2O$. Dry the EtOAc with $MgSO_4$, filter and evaporate the solvent in vacuo to obtain the title compound, $M^+=329$.

EXAMPLE 4

N-[2-[(N-(1-methylamino-2-nitroethylidene)amino]-ethyl]-3,5-diamino-6-chloropyrazine-2-carboxamide Step 1: Add N-(aminoethyl)-3,5-diamino-6-chloropyrazine-2-carboxamide (0.25 g) and 1,1-bis(methylthio)-2-nitroethylene (0.18 g) to isopropanol (10 ml) and heat at 70° C. for 18 hours. Evaporate the solvent.

Step 2: Dissolve the product of Step 1 (0.1 g) in EtOH (10 ml) and bubble methylamine gas through the solution until saturated (about 30 min.). Evaporate the solvent to obtain the title compound as a white solid, $M^+=330$.

EXAMPLE 5

N-(2-guanidinoethyl)-3,5-diamino-6-chloropyrazine-2-carboxamide hydrochloride trihydrate Step 1: Dissolve 3,5-diamino-6-chloropyrazine-2carboxylic acid (1 g) in warm DMF (15 ml). Cool to 25° C., add CDI (0.86 g) and stir under $N_2$ for about 30 minutes (a precipitate form). Add ethylenediamine (0.9 g) and stir the resultant solution overnight. Filter the reaction solution and evaporate the solvent. Purify by flash chromatography on silica gel (100 g) eluting with $CH_2Cl_2$:MeOH:$NH_4OH$ (70:30:1). Collect the desired fractions and evaporate the solvent to obtain N-(aminoethyl)-3,5-diamino-6-chloropyrazine-2-carboxamide.

Step 2: Dissolve the product of Step 1 (100 mg) and 2-methyl-2-thiopseudourea sulfate (122 mg) in water (0.5 ml) and MeOH (0.5 ml) and heat on a steam bath for 1 hour. If all the starting chloropyrazine is not reacted, add more pseudourea and repeat the procedure. Triturate the resulting residue in EtOH to obtain the sulfate salt of the title compound. Chromatograph the product on a high pressure reversed- phase prep C18 column (Dynamax), eluting with MeOH:$H_2O$ (40:60), 0.2% TFA, at 10 ml/min., followed by a C18 Magnum 20 column (Whatman), eluting with MeOH:$H_2O$ (30:70), 0.2% TFA. Dissolve the resultant residue in 1N HCl, evaporate the solvent, redissolve in water and lyophilize to obtain the title compound as a yellow solid, m.p. 100° (d), $M^+=272$.

EXAMPLE 6

N-[2-[2-cyano-3-(4-methoxycarbonylphenylmethyl)-guanidino]ethyl]-3,5-diamino-6-chloropyrazine-2-carboxamide, hemihydrate Step 1: Slurry dimethylcyanodithioimide (0.5 g) in MeOH (5 ml), add triethylamine (0.16 ml), add 4-methoxycarbonylbenzylamine (0.31 g) and stir for 2 hours. Dilute the reaction mixture with MeOH, filter and dry the precipitate.

Step 2: Slurry the product of Step 1 (0.27 g) and ethylenediamine (0.13 ml) in DMF (5 ml) and heat at 55° C. overnight, then at 65° C. for 8 hours. Evaporate the solvent to obtain a residue.

Step 3: Dissolve 3,5-diamino-6-chloropyrazine-2-carboxylic acid (0.2 g) in warm DMF (3 ml), cool to 25° C., add CDI (0.162 g) and stir for 1 hour. Add the product of Step 2 (0.28 g) in DMF (1 ml) and stir for 60 hours. Evaporate the solvent and titurate the resultant residue in EtOAc. Purify the residue by flash chromatography on silica gel (200 g), eluting with $CHCl_2$:MeOH:$N-H_4OH$ (95:5:1) to obtain the title compound as a white solid, m.p. 190°-195° C., $M^+=445$.

EXAMPLE 7

N-[2-[2-carbamoyl-3-(4-methoxycarbonylphenylmethyl)-guanidino]ethyl]-3,5-diamino-6-chloropyrazine-2-carboxamide, hydrochloride, pentahydrate Dissolve the product of Example 6 (100 mg) in TFA (10 ml) and allow to stand overnight. Evaporate the solvent and dry the resultant residue under high vacuum. Triturate the residue in 1N HCl, evaporate the solvent and dry under high vacuum at 60° C. overnight to obtain the title compound as a yellow solid, m.p. 140° C.(d), $M^+=463$.

EXAMPLE 8

N-[2-[(N-cyano)guanidino]ethyl]-3,5-diamino-6-chloropyrazine-2-carboxamide

Use a procedure similar to that described in Example 1, substituting ammonia for methylamine in Step 1 to obtain the title compound as a pale yellow solid, $M^+=297$.

EXAMPLE 9

N-[4-[(N'-carbamoyl-N''methyl)guanidino]butyl]-3,5-diamino-6-chloropyrazine-2-carboxyamide dihydrochloride dihydrate Use a procedure similar to that described in Example 3, Method 1, substituting the product of Example 2 as the starting material, to obtain the title compound as a hygroscopic orange solid, $M^+=357$.

The compounds of this invention are useful in view of their pharmacological properties. In particular, compounds of this invention possess activity as anti-hypertensive agents.

The compounds of this invention can be combined with pharmaceutical carriers to prepare well known pharmaceutical dosage forms suitable for oral or parenteral administration. Such pharmaceutical compositions are useful in the treatment of cardiovascular disorders and particularly mammalian hypertension.

The effective daily antihypertensive dose of the compounds of this invention will typically be in the range of about 0.01 to 1 mg/kg, preferably about 0.05 to 0.2, especially about 0.1 mg/kg mammalian weight, administered in single or divided doses. The exact dose to be administered is determined by the attending clinician and is dependent upon where the particular compound lies within the above quoted range, as well as upon the age, weight and condition of the individual.

Generally, in treating humans having hypertension, the compounds of this invention may be administered to patients in need of such treatment at a dose of about 0.5 to about 10 mg per patient generally given several (e.g., 1-4) times a day, thus giving a total daily dosage of from about 0.5 to about 40 mg per day.

The compounds of the present invention are preferably administered orally, e.g., in tablets or capsule form, but may also be administered parenterally, e.g., injectable solutions or suspensions. Also contemplated are mechanical delivery systems, e.g., transdermal dosage forms.

We claim:

1. A compound represented by the formula

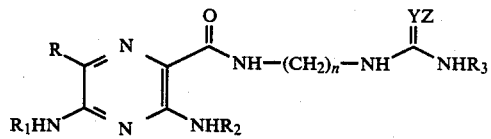

wherein
n is 2-6;
R is F, Cl, Br or I;
$R_1$ and $R_2$ are independently hydrogen or lower alkyl;
$R_3$ is hydrogen, lower alkyl, aryl, substituted aryl, heterorayl, substituted heteroaryl, lower alkylaryl, substituted lower alkylaryl, lower alkylheteroaryl, or substituted lower alkylheteroaryl wherein aryl is a $C_6$–$C_{10}$ carbocyclic aromatic single or fused ring, heteroaryl is a 5–6 membered aromatic ring wherein 1–3 ring members are selected from the group consisting of oxygen, nitrogen and sulfur, and wherein substituted aryl, substituted heteroaryl, substituted lower alkylaryl and substituted lower alkylheteroaryl have on the aryl or heteroaryl portions thereof 1–3 substitutents selected from the group consisting of lower alkyl, lower alkoxy, halogeno, amino, carboxy and lower alkoxy carbonyl;

Y is $=$CH— or $=$N—;

Z is hydrogen, cyano or carbamoyl when Y is $=$N—, and when Y is $=$CH—, Z is nitro;

and the pharmaceutically acceptable acid addition salts thereof.

2. A compound according to claim 1 wherein n is 2.

3. A compound according to claim 1 wherein Y is $=$N—.

4. A compound according to claim 1 wherein R is chloro or iodo.

5. A compound according to claim 1 wherein $R_1$ and $R_2$ are each hydrogen.

6. A compound according to claim 1 wherein $R_3$ is hydrogen or lower alkyl.

7. A compound according to claim 1 wherein Y is $=$N— and Z is cyano.

8. A compound according to claim 7 wherein n is 2.

9. A compound according to claim 8 wherein $R_1$ and $R_2$ are each hydrogen and $R_3$ is hydrogen or lower alkyl.

10. A compound according to claim 1 wherein Y is $=$CH— and Z is nitro.

11. A compound according to claim 10 wherein n is 2.

12. A compound according to claim 1 named:

N-[2-[(N'-methyl-N''-cyano)guanidino]ethyl]-3,5-diamino-6-chloropyrazine-2-carboxamide;

N-[2-[(N'-cyano)guanidino]ethyl]-3,5-diamino-6-chloropyrazine-2-carboxamide;

N-[2-[(N'-methyl-N''-cyano)guanidino]butyl]-3,5-diamino-6-chloropyrazine-2-carboxamide;

N-[2-[(N'-carbamoyl-N''-methyl)guanidino]ethyl]-3,5-diamino-6-chloropyrazine-2-carboxamide;

N-[2-[(N'-carbamoyl-N''-methyl)guanidino]butyl]-3,5-diamino-6-chloropyrazine-2-carboxamide;

N-[2-[(N-(1-methylamino-2-nitroethylidene)-amino]ethyl]-3,5-diamino-6-chloropyrazine-2-carboxamide;

N-(2-guanidinoethyl)-3,5-diamino-6-chloropyrazine-2-carboxamide;

N-[2-[2-cyano-3-(4-methoxycarbonylphenylmethyl)-guanidino]ethyl]-3,5-diamino-6-chloropyrazine-2-carboxamide; and N-[2-[2-carbamoyl-3-(4-methoxycarbonylphenylmethyl)guanidino]ethyl]-3,5-diamino-6-chloropyrazine-2-carboxamide.

13. A method of treating hypertension comprising administering an antihypertensive effective amount of a compound of claim 1 to a mammal in need of such treatment.

14. A pharmaceutical composition comprising an antihypertensive effective amount of a compound of claim 1 and a pharmaceutically acceptable carrier.

* * * * *